(12) United States Patent
Plaven et al.

(10) Patent No.: US 8,025,660 B2
(45) Date of Patent: Sep. 27, 2011

(54) UNIVERSAL FOOT SWITCH CONTACT PORT

(75) Inventors: Thomas Plaven, Littleton, CO (US); Robert L. Lohe, Shady Side, MD (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 12/620,666

(22) Filed: Nov. 18, 2009

(65) Prior Publication Data

US 2010/0068949 A1    Mar. 18, 2010

(51) Int. Cl.
   *A61B 18/04*    (2006.01)
(52) U.S. Cl. ............... 606/32; 606/1; 439/259; 439/263
(58) Field of Classification Search .................. 439/13,
   439/18–28, 217–218, 222, 223, 284, 292–295,
   439/259, 263; 279/2.01, 2.1, 2.18, 2.19,
   279/2.2, 35, 71–73, 75, 77, 106; 606/1, 32
   See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,883,198 A * | 4/1959 | Narumi ........................... 279/33 |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |

(Continued)

FOREIGN PATENT DOCUMENTS

DE    179607    3/1905

(Continued)

OTHER PUBLICATIONS

U.S. Appl. No. 10/406,690, filed Apr. 3, 2003.

(Continued)

*Primary Examiner* — Thomas J Sweet
*Assistant Examiner* — Samuel Candler

(57) ABSTRACT

A universal contact port for use in an electrosurgical generator is provided and includes a ring gear having a circular rim formed therein and defines a central rotational axis. The rim includes a series of teeth formed therearound. A plurality of spur gears are operatively engaged with the rim of the ring gear, each spur gear defining a longitudinal axis which is at least substantially parallel with the central rotational axis; and a plurality of rollers operatively associated with a respective spur gear, each roller defining a corporal axis. The corporal axis of each roller is parallel to and spaced from the longitudinal axis of the respective spur gear. The rollers define an opening therebetween. The opening is constricted by rotation of the ring gear in a first direction about the central rotational axis and expanded by rotation of the ring gear in a direction opposite to the first direction.

6 Claims, 8 Drawing Sheets

U.S. PATENT DOCUMENTS

| | | |
|---|---|---|
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |

| | | | | | |
|---|---|---|---|---|---|
| 5,024,668 A | 6/1991 | Peters et al. | 5,432,459 A | 7/1995 | Thompson |
| 5,044,977 A | 9/1991 | Vindigni | 5,433,739 A | 7/1995 | Sluijter et al. |
| 5,067,953 A | 11/1991 | Feucht | 5,436,566 A | 7/1995 | Thompson |
| 5,075,839 A | 12/1991 | Fisher et al. | 5,438,302 A | 8/1995 | Goble |
| 5,087,257 A | 2/1992 | Farin | 5,443,463 A | 8/1995 | Stern et al. |
| 5,099,840 A | 3/1992 | Goble et al. | 5,445,635 A | 8/1995 | Denen |
| 5,103,804 A | 4/1992 | Abele et al. | 5,451,224 A | 9/1995 | Goble et al. |
| 5,108,389 A | 4/1992 | Cosmescu | 5,452,725 A | 9/1995 | Martenson |
| 5,108,391 A | 4/1992 | Flachenecker | 5,454,809 A | 10/1995 | Janssen |
| 5,119,284 A | 6/1992 | Fisher et al. | 5,458,597 A | 10/1995 | Edwards et al. |
| 5,122,137 A | 6/1992 | Lennox | 5,462,521 A | 10/1995 | Brucker et al. |
| 5,133,711 A | 7/1992 | Hagen | 5,472,441 A | 12/1995 | Edwards et al. |
| 5,151,102 A | 9/1992 | Kamiyama et al. | 5,472,443 A | 12/1995 | Cordis et al. |
| 5,152,762 A | 10/1992 | McElhenney | 5,474,464 A | 12/1995 | Drewnicki |
| 5,157,603 A | 10/1992 | Scheller et al. | 5,480,399 A | 1/1996 | Hebborn |
| 5,160,334 A | 11/1992 | Billings et al. | 5,483,952 A | 1/1996 | Aranyi |
| 5,161,893 A | 11/1992 | Shigezawa et al. | 5,485,312 A | 1/1996 | Horner et al. |
| 5,167,658 A | 12/1992 | Ensslin | 5,496,312 A | 3/1996 | Klicek |
| 5,167,659 A | 12/1992 | Ohtomo et al. | 5,496,313 A | 3/1996 | Gentelia et al. |
| 5,190,517 A | 3/1993 | Zieve et al. | 5,496,314 A | 3/1996 | Eggers |
| 5,196,008 A | 3/1993 | Kuenecke | 5,500,012 A | 3/1996 | Brucker et al. |
| 5,196,009 A | 3/1993 | Kirwan, Jr. | 5,500,616 A | 3/1996 | Ochi |
| 5,201,900 A | 4/1993 | Nardella | 5,511,993 A | 4/1996 | Yamada et al. |
| 5,207,691 A | 5/1993 | Nardella | 5,514,129 A | 5/1996 | Smith |
| 5,230,623 A | 7/1993 | Guthrie et al. | 5,520,684 A | 5/1996 | Imran |
| 5,233,515 A | 8/1993 | Cosman | 5,531,774 A | 7/1996 | Schulman et al. |
| 5,234,427 A | 8/1993 | Ohtomo et al. | 5,534,018 A | 7/1996 | Wahlstrand et al. |
| 5,249,121 A | 9/1993 | Baum et al. | 5,536,267 A | 7/1996 | Edwards et al. |
| 5,249,585 A | 10/1993 | Turner et al. | 5,540,677 A | 7/1996 | Sinofsky |
| 5,254,117 A | 10/1993 | Rigby et al. | 5,540,681 A | 7/1996 | Strul et al. |
| RE34,432 E | 11/1993 | Bertrand | 5,540,682 A | 7/1996 | Gardner et al. |
| 5,267,994 A | 12/1993 | Gentelia et al. | 5,540,683 A | 7/1996 | Ichikawa |
| 5,267,997 A | 12/1993 | Farin | 5,540,684 A | 7/1996 | Hassler, Jr. |
| 5,281,213 A | 1/1994 | Milder et al. | 5,541,376 A | 7/1996 | Ladtkow et al. |
| 5,282,840 A | 2/1994 | Hudrlik | 5,545,161 A | 8/1996 | Imran |
| 5,290,283 A | 3/1994 | Suda | 5,556,396 A | 9/1996 | Cohen et al. |
| 5,295,857 A | 3/1994 | Toly | 5,558,671 A | 9/1996 | Yates |
| 5,300,068 A | 4/1994 | Rosar et al. | 5,562,720 A | 10/1996 | Stern et al. |
| 5,300,070 A | 4/1994 | Gentelia | 5,569,242 A | 10/1996 | Lax et al. |
| 5,304,917 A | 4/1994 | Somerville | 5,571,147 A | 11/1996 | Sluijter et al. |
| 5,318,563 A | 6/1994 | Malis et al. | 5,573,533 A | 11/1996 | Strul |
| 5,323,778 A | 6/1994 | Kandarpa et al. | 5,584,830 A | 12/1996 | Ladd et al. |
| 5,324,283 A | 6/1994 | Heckele | 5,588,432 A | 12/1996 | Crowley |
| 5,330,518 A | 7/1994 | Neilson et al. | 5,596,466 A | 1/1997 | Ochi |
| 5,334,183 A | 8/1994 | Wuchinich | 5,599,344 A | 2/1997 | Paterson |
| 5,334,193 A | 8/1994 | Nardella | 5,599,345 A | 2/1997 | Edwards et al. |
| 5,341,807 A | 8/1994 | Nardella | 5,599,348 A | 2/1997 | Gentelia et al. |
| 5,342,356 A | 8/1994 | Ellman | 5,605,150 A | 2/1997 | Radons et al. |
| 5,342,357 A | 8/1994 | Nardella | 5,609,560 A | 3/1997 | Ichikawa et al. |
| 5,342,409 A | 8/1994 | Mullett | 5,613,966 A | 3/1997 | Makower et al. |
| 5,346,406 A | 9/1994 | Hoffman et al. | 5,620,481 A | 4/1997 | Desai et al. |
| 5,346,491 A | 9/1994 | Oertli | 5,626,575 A | 5/1997 | Crenner |
| 5,348,554 A | 9/1994 | Imran et al. | 5,628,745 A | 5/1997 | Bek |
| 5,369,567 A | 11/1994 | Furuta et al. | 5,628,771 A | 5/1997 | Mizukawa et al. |
| 5,370,645 A | 12/1994 | Klicek et al. | 5,643,330 A | 7/1997 | Holsheimer et al. |
| 5,370,672 A | 12/1994 | Fowler et al. | 5,647,869 A | 7/1997 | Goble et al. |
| 5,370,675 A | 12/1994 | Edwards et al. | 5,647,871 A | 7/1997 | Levine et al. |
| 5,372,596 A | 12/1994 | Klicek et al. | 5,651,780 A | 7/1997 | Jackson et al. |
| 5,383,874 A | 1/1995 | Jackson | 5,658,322 A | 8/1997 | Fleming |
| 5,383,876 A | 1/1995 | Nardella | 5,660,567 A | 8/1997 | Nierlich et al. |
| 5,383,917 A | 1/1995 | Desai et al. | 5,664,953 A | 9/1997 | Reylek |
| 5,385,148 A | 1/1995 | Lesh et al. | 5,674,217 A | 10/1997 | Wahlstrom et al. |
| 5,400,267 A | 3/1995 | Denen et al. | 5,678,568 A | 10/1997 | Uchikubo et al. |
| 5,403,311 A | 4/1995 | Abele et al. | 5,681,307 A | 10/1997 | McMahan |
| 5,403,312 A | 4/1995 | Yates et al. | 5,685,840 A | 11/1997 | Schechter et al. |
| 5,409,000 A | 4/1995 | Imran | 5,688,267 A | 11/1997 | Panescu et al. |
| 5,409,485 A | 4/1995 | Suda | 5,693,042 A | 12/1997 | Bioarski et al. |
| 5,413,573 A | 5/1995 | Koivukangas | 5,693,078 A | 12/1997 | Desai et al. |
| 5,414,238 A | 5/1995 | Steigerwald et al. | 5,694,304 A | 12/1997 | Telefus et al. |
| 5,417,719 A | 5/1995 | Hull et al. | 5,695,494 A | 12/1997 | Becker |
| 5,422,567 A | 6/1995 | Matsunaga | 5,696,351 A | 12/1997 | Benn et al. |
| 5,422,926 A | 6/1995 | Smith et al. | 5,696,441 A | 12/1997 | Mak et al. |
| 5,423,808 A | 6/1995 | Edwards et al. | 5,697,925 A | 12/1997 | Taylor |
| 5,423,809 A | 6/1995 | Klicek | 5,697,927 A | 12/1997 | Imran et al. |
| 5,423,810 A | 6/1995 | Goble et al. | 5,702,386 A | 12/1997 | Stern et al. |
| 5,423,811 A | 6/1995 | Imran et al. | 5,702,429 A | 12/1997 | King |
| 5,425,704 A | 6/1995 | Sakurai et al. | 5,707,369 A | 1/1998 | Vaitekunas et al. |
| 5,429,596 A | 7/1995 | Arias et al. | 5,712,772 A | 1/1998 | Telefus et al. |
| 5,430,434 A | 7/1995 | Lederer et al. | 5,713,896 A | 2/1998 | Nardella |

| Patent No. | Date | Name |
|---|---|---|
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkenbaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |

| | | |
|---|---|---|
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble et al. |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |

| Patent No. | Date | Name |
|---|---|---|
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,582,084 B2 | 9/2009 | Swanson et al. |
| 2002/0029036 A1 | 3/2002 | Goble et al. |
| 2003/0181898 A1 | 9/2003 | Bowers |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0130104 A1* | 7/2004 | Sundkvist ................. 279/35 |
| 2004/0143263 A1 | 7/2004 | Schechter et al. |
| 2004/0172016 A1 | 9/2004 | Bek et al. |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0291178 A1 | 12/2006 | Shih |
| 2006/0293649 A1 | 12/2006 | Lorang et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0203481 A1 | 8/2007 | Gregg et al. |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0082096 A1 | 4/2008 | Shores et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2009/0234350 A1 | 9/2009 | Behnke et al. |
| 2009/0237169 A1 | 9/2009 | Orszulak |
| 2009/0248003 A1 | 10/2009 | Orszulak |
| 2009/0259224 A1 | 10/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |

| | | |
|---|---|---|
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 5/2006 |
| EP | 880220 | 6/2006 |
| EP | 1681026 | 7/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2154881 | 9/1985 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060849 | 7/2005 |
| WO | WO2006/050888 | 5/2006 |
| WO | WO2006/105121 | 10/2006 |

OTHER PUBLICATIONS

U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.
U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.

Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2; (Mar. 2005) pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Aced Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.
Canadian Office Action dated Oct. 7, 2010.
US 6,878,148, 04/2005, Goble et al. (withdrawn)

* cited by examiner

UNIVERSAL FOOT SWITCH CONTACT PORT

CROSS-REFERENCE TO RELATED APPLICATION

The present application claims the benefit of and priority to U.S. application Ser. No. 11/129,985, filed on May 16, 2005; U.S. Provisional Application 60/618,439, filed on Oct. 13, 2004, and U.S. Provisional Application 60/666,832, filed on Mar. 31, 2005, the entire contents of each of which being incorporated herein by reference.

BACKGROUND

1. Technical Field

The present disclosure relates to electrosurgical instrument systems and, more particularly, to a universally adaptable contact port for selectively connecting electrosurgical instruments to electrosurgical generators.

2. Background

Electrosurgical instrument systems have become widely used by surgeons in recent years. Accordingly, a need has developed for equipment that is easy to handle and operate, is reliable and is safe. By and large, most electrosurgical instrument systems typically include a hand-held electrosurgical instrument or pencil electrically connected to a source of electrosurgical energy (e.g., an electrosurgical generator). When activated, the electrosurgical instrument transfers electrosurgical energy, e.g., radio-frequency (RF) electrical energy, to a tissue site to treat tissue. The electrosurgical energy is returned to the electrosurgical generator via a return electrode (i.e., for use with a bipolar system) or a return electrode pad positioned under a patient (i.e., for use with a monopolar system configuration). The waveforms produced by the electrosurgical generator yield a predetermined electrosurgical effect which can be used to cauterize, ablate, coagulate or seal tissue depending upon a particular surgical purpose.

Electrosurgical instrument systems are typically provided with electrosurgical activation components (e.g., a remote hand switch or foot switch), operatively connected (e.g., hard wired) to the electrosurgical generator, which allows a user to selectively control the application of the electrosurgical energy to the electrosurgical instrument. In the past, surgeons connected the electrical components or instruments using so-called "banana plugs" or "flying leads". Recently, electrosurgical instrument systems are increasingly being provided with coupling and/or connecting systems (e.g., a plug) for removably connecting the electrosurgical instrument components and/or the electrosurgical activation components to the electrosurgical generator. Typically, the electrosurgical instrument and/or activation component is provided with a so called "male" connector while the electrosurgical generator is provided with the corresponding "female" receptacle.

As can be appreciated, electrosurgical instruments and/or activation components manufactured by different manufacturers are provided with active contacts having different diameters, e.g., from about 2 mm to about 10 mm making it difficult to use particular instruments with particular generators. As such, components can only be plugged into receptacles having correspondingly sized apertures provided therein or the surgeon has to couple an adapter to the instrument prior to use. Depending upon the number of instruments being used with a particular generator might make the task of providing an appropriate adapter time consuming.

Accordingly, a need exists for a universal contact port for electrosurgical generators which allows components having various sized active contacts to be selectively connected thereto.

SUMMARY

According to an embodiment, a universal contact port for use in an electrosurgical generator is provided. The contact port includes a ring gear having a circular rim formed therein and defining a central rotational axis, the rim including a series of teeth formed therearound; a plurality of spur gears operatively engaged with the rim of the ring gear, each spur gear defining a longitudinal axis which is at least substantially parallel with the central rotational axis; and a plurality of rollers operatively associated with a respective spur gear, each roller defining a corporal axis. The corporal axis of each roller is parallel to and spaced from the longitudinal axis of the respective spur gear. The rollers define an opening therebetween. The opening is constricted by rotation of the ring gear in a first direction about the central rotational axis and expanded by rotation of the ring gear in a direction opposite to the first direction.

The universal contact port may further include a plurality of shafts for eccentrically supporting each roller. Each shaft may include a first end operatively associated with a respective spur gear and a second end operatively associated with the electrosurgical generator.

It is envisioned that three rollers are provided. The shafts of the three rollers may be equally spaced from one another. The opening is at a minimum when the rollers are in contact with one another. The opening is at a maximum when the corporal axes of the rollers are positioned radially outward of the longitudinal axes of the shafts relative to the central axis of the ring gear. The opening is expandable to receive active contacts of varying diameters therein. The opening is sizable to receive contacts having cross-sectional diameters from about 2 mm to about 10 mm.

The rollers may be fabricated from electrically conductive material. The shafts, the spur gears and the ring gears may be fabricated from electrically conductive material.

The ring gear and the spur gears define a planetary gear system.

The universal contact port further includes at least one biasing member operatively associated with at least one of the ring gear, at least one of the spur gears and at least one of the rollers for urging the rollers into contact with one another.

According to another aspect of the present disclosure, a universal contact port for receiving contacts of various cross-sectional dimensions and cross-sectional profiles of an electrosurgical component is provided. The universal contact port includes a plurality of rollers each defining a corporal axis, the corporal axes being at least substantially parallel to one another; and a plurality of shafts eccentrically supporting a respective roller, each shaft defining a longitudinal axis, wherein each corporal axis is spaced a radial distance from a respective longitudinal axis and wherein the rollers are rotatable about the longitudinal axes. The rollers define an opening therebetween. The opening is expandable and constrictable upon rotation of the rollers about the longitudinal axes. The contact port can accommodate receipt of contacts, from electrosurgical components, of varying cross-sectional diameter therein.

The opening may have a minimum cross-sectional dimension when the rollers are in contact with one another. The opening may have a maximum cross-sectional profile when the corporal axes of the rollers are radially aligned with respective longitudinal axes of the shafts.

The universal contact port further includes a spur gear operatively associated with an end of each of the shafts; and a drive member operatively associated with all the spur gears for transmitting rotation to each of the spur gear simultaneously. The drive member may be a ring gear surrounding and inter-connecting each spur gear.

The contact port can accommodate receipt of contacts of varying cross-sectional profiles therein.

The universal contact port may further include at least one biasing member operatively associated with at least one of the ring gear, at least one of the spur gears and at least one of the rollers, wherein the biasing member urges the rollers into contact with one another.

The opening may be sizable to receive contacts having cross-sectional diameters from about 2 mm to about 10 mm.

According to yet another aspect of the present disclosure, an electrosurgical system including an electrosurgical generator, and an electrosurgical component including an active contact for operatively connecting the electrosurgical component to the electrosurgical generator is provided. The improvement includes a contact port operatively associated with the electrosurgical generator for receiving active contacts of varying cross-sectional diameters therein. The contact port includes a plurality of rollers each defining a corporal axis, the corporal axes being at least substantially parallel to one another; and a plurality of shafts eccentrically supporting a respective roller, each shaft defining a longitudinal axis, wherein each corporal axis is spaced a radial distance from a respective longitudinal axis and wherein the rollers are rotatable about the longitudinal axes. The rollers define an opening therebetween, wherein the opening is expandable and constrictable upon rotation of the rollers about their respective longitudinal axes.

The opening may have a minimum cross-sectional dimension when the rollers are in contact with one another. The opening may have a maximum cross-sectional profile when the corporal axes of the rollers are radially aligned with respective longitudinal axes of the shafts.

The contact port further includes a spur gear operatively associated with an end of each of the shafts; and a drive member operatively associated with all the spur gears for transmitting rotation to each of the spur gear simultaneously. The drive member may be a ring gear surrounding and interconnecting each spur gear.

The contact port further includes at least one biasing member operatively associated with at least one of the ring gear, at least one of the spur gears and at least one of the rollers. The biasing member urges the rollers into contact with one another.

The electrosurgical component may be a foot switch.

The rollers of the contact port may be biased to a position wherein the opening is in a constricted condition. Each roller may include an electrical contact pad operatively disposed on a surface thereof.

The contact port may further include an actuator rod operatively associated with the rollers. Accordingly, movement of the actuator rod in a first direction moves the rollers in a direction so as to expand the opening therebetween, and movement of the actuator rod in a second direction moves the rollers in a direction so as to constrict the opening therebetween. The actuator rod includes a distal end projecting from the electrosurgical generator, and a proximal end pivotably supporting a first end of a lever. The contact port may further include a pusher member pivotably connected to a second end of the lever, wherein the lever pivots about a point located between the first and second ends thereof. Movement of the actuator rod in a first direction results in movement of the pusher member in a direction opposite to the first direction.

A distal end of the pusher member may operatively engage the rollers. Accordingly, movement of the pusher member in a direction towards the rollers results in radial movement of the rollers and radial expansion of the opening therebetween.

The electrosurgical system further includes an electrical lead electrically connected to each roller. The electrosurgical system further includes a housing configured and dimensioned to operatively retain the contact port therein.

According to still another aspect of the present disclosure, a universal contact port for use in an electrosurgical generator is provided. The contact port includes a housing defining an aperture for registration with an aperture formed in the electrosurgical generator; a plurality of rollers pivotally supported in the housing and pivotable about a pivot axis, each roller defining a corporal axis spaced a distance from the pivot axis, wherein the corporal axes of the rollers are parallel to one another, the rollers define an opening therebetween, wherein the opening is constricted by rotation of the rollers in a first direction about their respective pivot axes and expanded by rotation of the rollers in a second direction about their respective pivot axes; an actuator rod slidably supported in the housing, the actuator rod including a distal end extending from a distal end of the housing and projecting from the electrosurgical generator, and a proximal end projecting from a proximal end of the housing; a pusher member operatively associated with the housing, the pusher member including a distal in operative engagement with the rollers, wherein movement of the pusher member in a first direction causes the rollers to radially expand and the opening therebetween to radially expand, and wherein movement of the pusher member in a second direction causes the rollers to radially retract and the opening therebetween to radially constrict; and a lever pivotally interconnecting the proximal end of the actuator rod to a proximal end of the pusher member, wherein the lever is pivotally connected to the housing, wherein movement of the actuator rod in a first direction results in movement of the pusher member in the first direction and movement of the actuator rod in a second direction results in movement of the pusher member in the second direction.

The actuator rod may be biased in the second direction. The rollers may be biased to a radially constricted condition.

Each roller may include an electrical contact pad disposed on a surface thereof. The electrical contact pads may be positioned on the rollers so as to engage a contact of an electrosurgical accessory when the contact of the electrosurgical accessory is inserted into the opening between the rollers and the rollers constricted onto the contact of the electrosurgical accessory. Each roller may be configured for electrical connection with a respective electrical lead, and wherein each contact pad is in electrical communication with a respective electrical lead.

BRIEF DESCRIPTION OF THE DRAWINGS

Various embodiments of the present disclosure are described with reference to the following drawing figures. It should be understood, however, that the drawings are designed for the purpose of illustration only and not as a definition of the limits of the invention.

DETAILED DESCRIPTION

Figure 1:
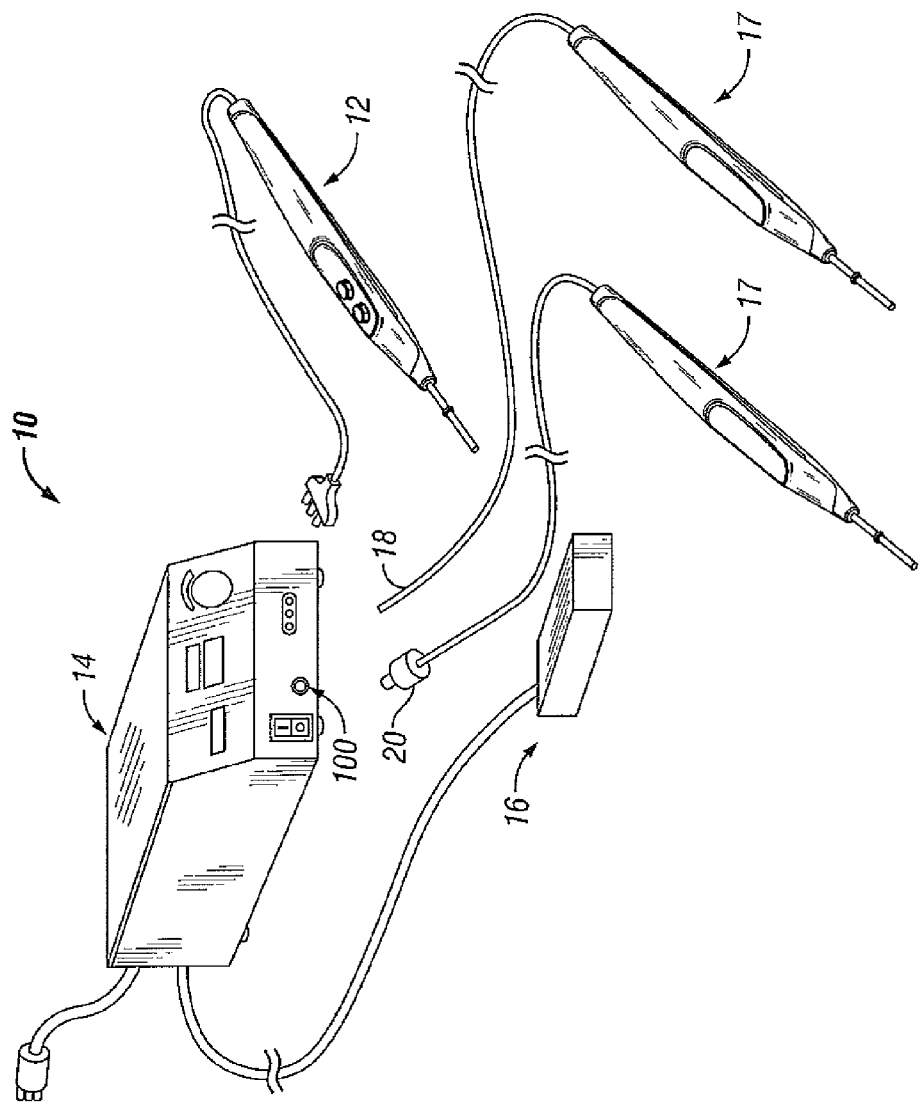
FIG. 1 is a schematic illustration of an electrosurgical instrument system including a universal contact port according to the present disclosure.

Embodiments of the presently disclosed universal contact port for electrosurgical generators are described in detail herein with reference to the drawing figures wherein like reference numerals identify similar or identical elements. In the drawings and in the description which follows, the term "proximal", as is traditional, will refer to the end of the apparatus and/or device which is closest to the operator, while the term "distal" will refer to the end of the apparatus and/or device which is furthest from the operator.

Referring initially to FIG. 1, there is seen a perspective view of an electrosurgical instrument system in accordance with an exemplary embodiment of the present disclosure, generally indicated as reference numeral 10. Electrosurgical instrument system 10 includes an electrosurgical instrument 12 (e.g., an electrosurgical pencil) which is electrically connectable to a source of electrosurgical energy 14 (e.g., an electrosurgical generator).

By way of example only, electrosurgical generator 14 may be any one of the following, or equivalents thereof: the "FORCE FX™", "FORCE 2™" or "FORCE 4™" generators manufactured by Valleylab, Inc. of Boulder, Colo., a division of Tyco Healthcare Group LP. It is contemplated that electrosurgical generator 14 can be preset to selectively provide an appropriate RF signals (e.g., about 1 to 300 watts) for a particular surgical procedure. Electrosurgical generator 14 may be adapted to automatically configure itself to transmit particular RF signals depending on the particular electrosurgical instrument connected thereto.

Electrosurgical instrument system 10 can further include a foot switch 16 which selectively couples to electrosurgical generator 14. Electrosurgical generator 14 includes a universal contact port 100 operatively associated therewith. Contact port 100 is configured to receive contacts 18 or plugs 20 of a footswitched accessory 17. As understood herein, a footswitched accessory is a surgical device that requires a separate foot switch 16 to activate electrosurgical generator 14 to provide the RF energy which is delivered to the patient through the footswitched accessory 17. A footswitched accessory 17 is similar to electrosurgical instrument 12 except that electrosurgical instrument 12 is handswitched as opposed to footswitched. In particular, contact port 100 is configured to accommodate receipt of and establish acceptable electrical connection with contacts 18 of varying diameters, e.g., from about 2 mm to about 10 mm.

With reference to FIGS. 2-5, contact port 100 functions in the manner of a planetary and/or epicyclic gear system. Contact port 100 includes a drive member in the form of a ring or sun gear 110, a plurality of spur gears 120a, 120b, 120c (i.e., planet gears) operatively associated with ring gear 110, and a plurality of rollers 130a, 130b, 130c operatively associated with a respective one of the plurality of spur gears 120a, 120b, 120c.

Ring gear 110 includes an annular body 112 defining a circular inner rim 114 having a plurality of gear teeth 116 formed therein. Gear teeth 116 extend at least partially, preferably entirely, around the perimeter of inner rim 114. Inner rim 114 of ring gear 110 defines a central rotational axis "X".

While a ring gear 100 surrounding spur gears 120 is shown, it is envisioned that a ring gear disposed radially internally of the spur gears is possible and within the scope of the present disclosure (not shown). In addition, while a rigid ring gear is shown, it is envisioned and within the scope of the present disclosure that a belt, band or chain (not shown) interconnecting all of the spur gears is also possible. It is further envisioned that each spur gear 120 may be configured for independent rotation. Preferably, the system is configured to result in simultaneous uniform rotation of spur gears 120 to assume consistent and reliable electro-mechanical connection of contact 18 or plug 20.

Preferably, contact port 100 includes three spur gears 120a, 120b and 120c. While three spur gears are shown, it is envisioned that any number of spur gears can be provided depending on the particular purpose. Preferably, spur gears 120a, 120b and 120c are each supported on a first end 122 of a respective shaft 124a, 124b and 124c. Each spur gear 120a, 120b and 120c includes a series of teeth 128 for meshing with and/or otherwise inter-engaging with gear teeth 116 of ring gear 110. Spur gears 120a, 120b and 120c are preferably fixedly connected to respective shafts 124a, 124b and 124c. In this manner, as will be discussed in greater detail below, as spur gears 120a, 120b and 120c are rotated, shafts 124a, 124b and 124c are also rotated.

Preferably, a second end 126 of each shaft 124a, 124b and 124c is rotatably supported and/or is otherwise operatively associated with the inner surface of electrosurgical generator 14. Each shaft 124a, 124b and 124c defines a central longitudinal axis "Xa, Xb and Xc", respectively. Preferably, central longitudinal axes "Xa, Xb and Xc" are at least substantially parallel with central axis "X" of ring gear 110.

Shafts 124a, 124b and 124c are positioned such that spur gears 120a, 120b and 120c are preferably equi-distant from one another, e.g., spaced from one another by about 120°.

Contact port 100 includes three rollers 130a, 130b and 130c, eccentrically supported on a respective shaft 124a, 124b and 124c. Rollers 130a, 130b and 130c define an opening 140 therebetween.

Rollers 130a, 130b and 130c are substantially cylindrical in configuration and define central corporal axes "Wa, Wb and Wc", respectively. Each central corporal axis "Wa, Wb and Wc" of roller 130a, 130b and 130c is parallel to and preferably offset a radial distance from the central longitudinal axis Xa, Xb and Xc of each respective shaft 124a, 124b and 124c. In operation, as will be discussed in greater detail below, as shafts 124a, 124b and 124c are rotated about respective central axes "Xa, Xb and Xc", rollers 130a, 130b and 130c are approximated toward one another to constrict opening 140 (or space apart from one another to expand opening 140).

Figure 2:
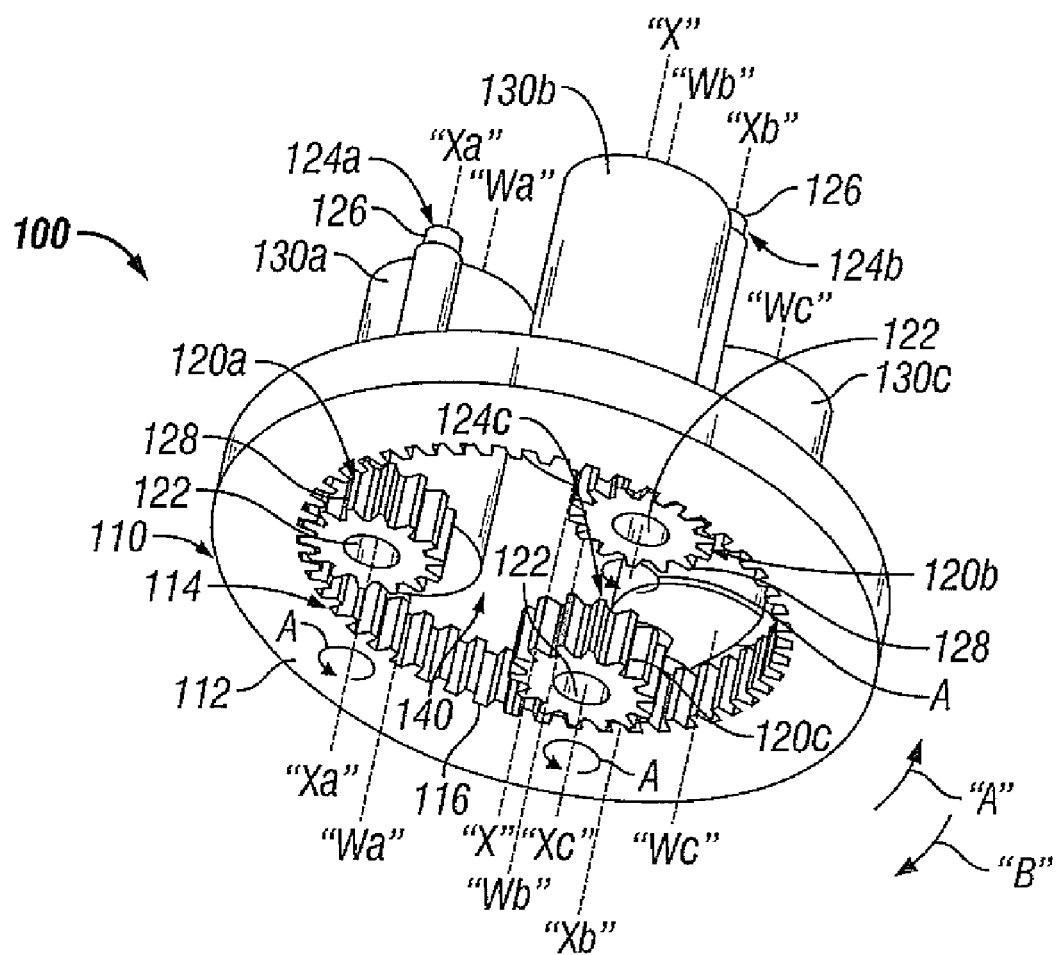
FIG. 2 is an enlarged perspective view of the universal contact port of the present disclosure.
Figure 3:
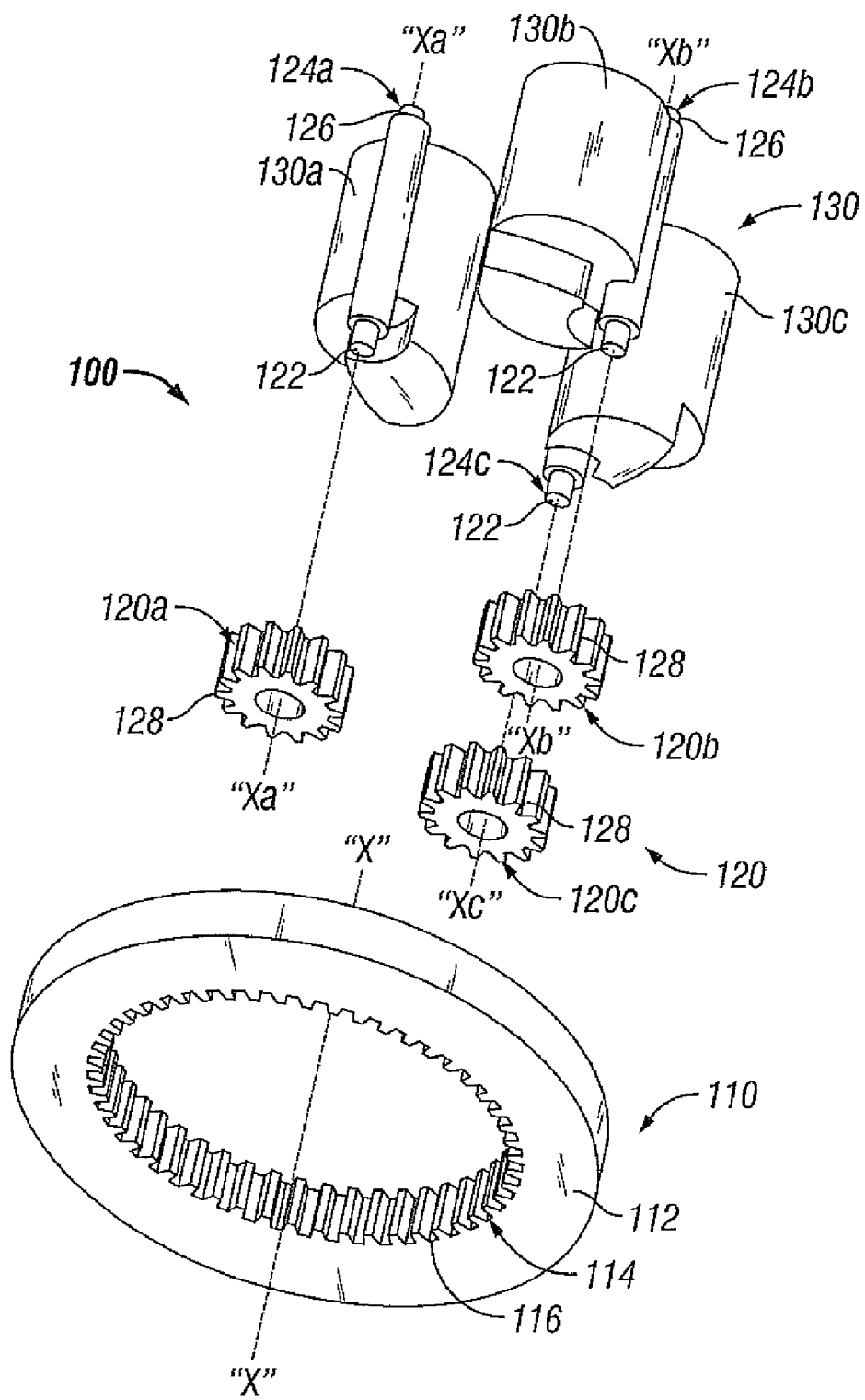
FIG. 3 is an enlarged exploded perspective view of the universal contact port of FIG. 2.
Figure 4:
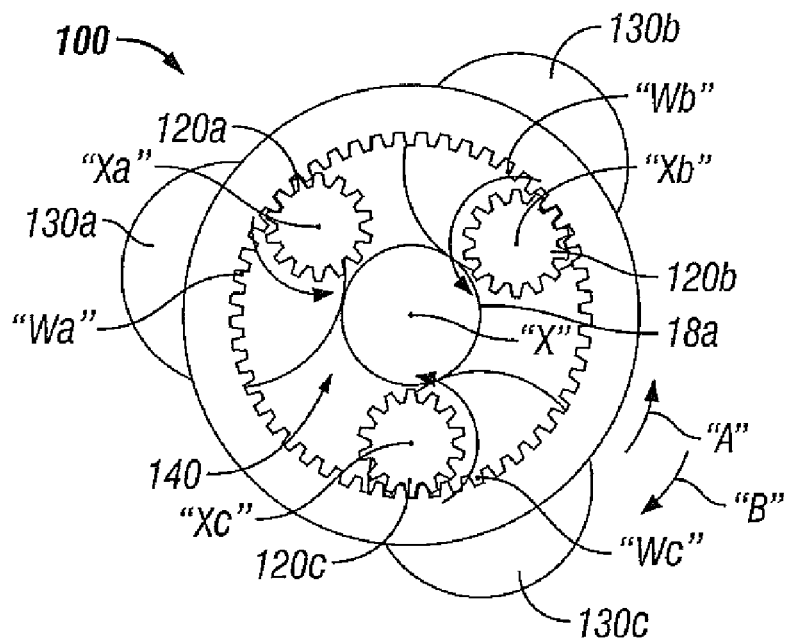
FIG. 4 is a schematic elevational view of universal contact port of FIGS. 2 and 3, illustrating the inter-engagement of the contact port with an active contact having a relatively large cross-sectional diameter.
Figure 5:
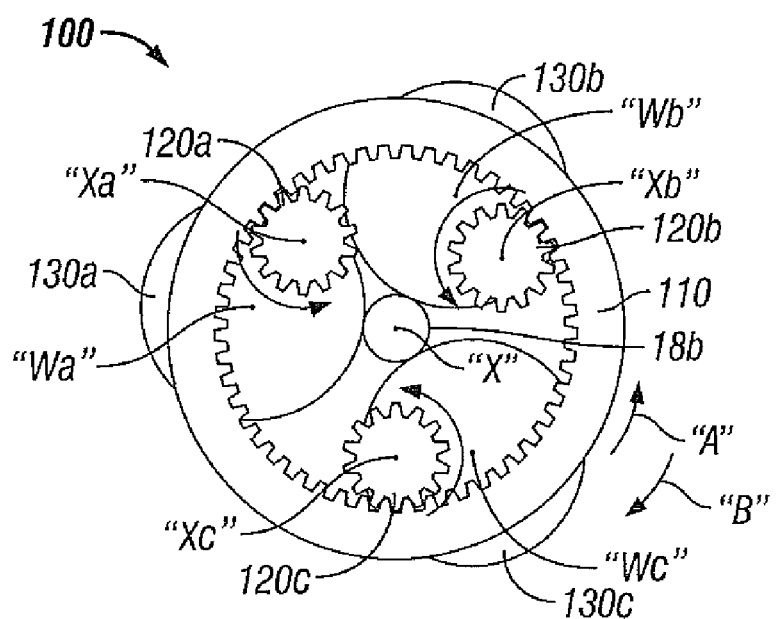
FIG. 5 is a schematic elevational view of the universal contact port of FIGS. 2-4, illustrating the inter-engagement of the contact port with an active contact having a relatively small cross-sectional diameter.

In operation, as seen in FIGS. 2, 4 and 5, as ring gear 110 is rotated about central axis "X" in the direction of arrow "A" (i.e., in a counter-clockwise direction), each spur gear 120a, 120b and 120c rotates about respective axes "Xa, Xb and Xc", in direction "A" (i.e., in a counter-clockwise direction). In so doing, rollers 130a, 130b and 130c are approximated toward one another thereby constricting opening 140. Additionally, as ring gear 110 is rotated about central axis "X" in the direction of arrow "B" (i.e., in a clockwise direction), each spur gear 120a, 120b and 120c rotates about respective axes "Xa, Xb and Xc", in direction "B" (i.e., in a clockwise direction). In so doing, rollers 130a, 130b and 130c separate from one another thereby causing opening 140 to expand.

It should be apparent to one skilled in the art that if ring gear 110 is continually rotated about central axis "X", in direction "B", rollers 130a, 130b and 130c will continue to rotate about axes "Xa, Xb and Xc" until the eccentricities of rollers 130a, 130b and 130c revert to restricting opening 140.

With reference to FIG. 4, prior to insertion of contact 18 or plug 20 into opening 140, ring gear 110 is caused to be rotated in direction "B" to expand opening 140 to a dimension sufficient to receive contact 18 or plug 20 therein. Following insertion of a contact having a relatively large cross-sectional diameter into opening 140, e.g., contact 18a, ring gear 110 is rotated (or caused to be rotated) in direction "A" to thereby constrict opening 140. In other words, ring gear 110 is rotated in direction "A" until rollers 130a, 130b and 130c engage contact 18a.

With reference to FIG. 5, following insertion of a contact having a relatively small cross-sectional diameter into opening 140, e.g., contact 18b, ring gear 110 is rotated (or caused to be rotated) in direction "A" the thereby constrict opening 140. As can be appreciated, since contact 18b has a relatively smaller cross-sectional diameter than contact 18a, ring gear 110 is necessarily rotated further in direction "A" until rollers 130a, 130b and 130c properly engage contact 18b.

Preferably, contact port 100 can accommodate receipt of contacts 18 having diameters from about 2 mm to about 10 mm. It is envisioned that contact 18 may include diameters which are in a range defined from when rollers 130a, 130b and 130c are almost in substantial contact with one another to a diameter when axes "Wa, Wb and Wc" of rollers 130a, 130b and 130c are spaced the greatest radial distance from central axis "X" of ring gear 110.

In other words, the acceptable diameter of contact 18 is at a minimum when rollers 130a, 130b and 130c are in contact with one another. The acceptable diameter of contact 18 is at a maximum when corporal axes "Wa, Wb and Wc" of rollers 130a, 130b and 130c are positioned radially outward of longitudinal axes "Xa, Xb and Xc" of shafts 124a, 124b and 124c relative to central rotational axis "X".

Preferably, rollers 130a, 130b and 130c are biased toward one another by a biasing member, e.g., a spring, (not shown). In this manner, rollers 130a, 130b and 130c can be urged, against the force of the biasing member, apart from one another. Then, following insertion of contact 18 into opening 140, rollers 130a, 130b and 130c automatically return or bias toward one another as a result of force of the biasing member. The force of the biasing member can be applied to ring gear 110, to at least one of spur gears 120a, 120b and 120c, and/or to at least one of rollers 130a, 130b and 130c.

Contact port 100 preferably includes a button, lever or mechanism (not shown) which drives ring gear 110 against the force of the biasing member to thereby expand opening 140. Following insertion of contact 18 into opening 140 the button is released and the rollers constrict around contact 18, as described in detail above. In order to remove contact 18, the button is depressed in order to rotate ring gear 110 in the appropriate direction to cause opening 140 to expand thereby electro-mechanically releasing. By way of example only, the button may include a worm gear or the like formed in a proximal end thereof which engages or meshes with a complementary gear formed along the outer edge of ring gear 110. Accordingly, when the button is pushed in ring gear 110 is rotated in the appropriate direction to thereby expand opening 140. It is further envisioned that the button may be spring biased to the ejected condition. In this manner, when the button is released, the button will be forced back to the non-pushed-in condition, thereby constricting opening 140.

While a planetary gear system is preferred, it is envisioned that a system of pins and slider elements may be used to cause rollers 130a, 130b and 130c to rotate. For example, this alternate system may include a link member having a first end pivotally connected to the housing of electrosurgical generator 14 and a second end operatively connected to a respective roller 130a, 130b and 130c. Desirably, each link may pivot about its first end to impart the desired motion to rollers 130a, 130b and 130c. The links may be joined together by pins operatively connected thereto that slide or translate in a groove or slot formed in the link. In this manner, as the pins are moved, the links are moved in concert to expand or constrict opening 140.

Preferably, rollers 130a, 130b and 130c are fabricated from electrically conductive material, e.g., stainless steel, and are each disposed in electrical connection with electrosurgical generator 14. In this manner, when contact 18 is inserted into contact port 100, electrical connection is established between contact 18 of plug 20 and electrosurgical generator 14, via rollers 130a, 130b and 130c. Alternatively, electrical connection can be established through the gear train.

Contact port 100 eliminates the need to use an adapter to establish a connection between a plug having a contact of a given dimension and a plug receptacle having a dimension different from that of the contact.

Moreover, contact port 100 allows for electrical connections to be established with contacts having any number of cross-sectional profiles, including and not limited to, square, rectangle, L-shaped, elliptical, oblong, circular, etc.

Figure 6:
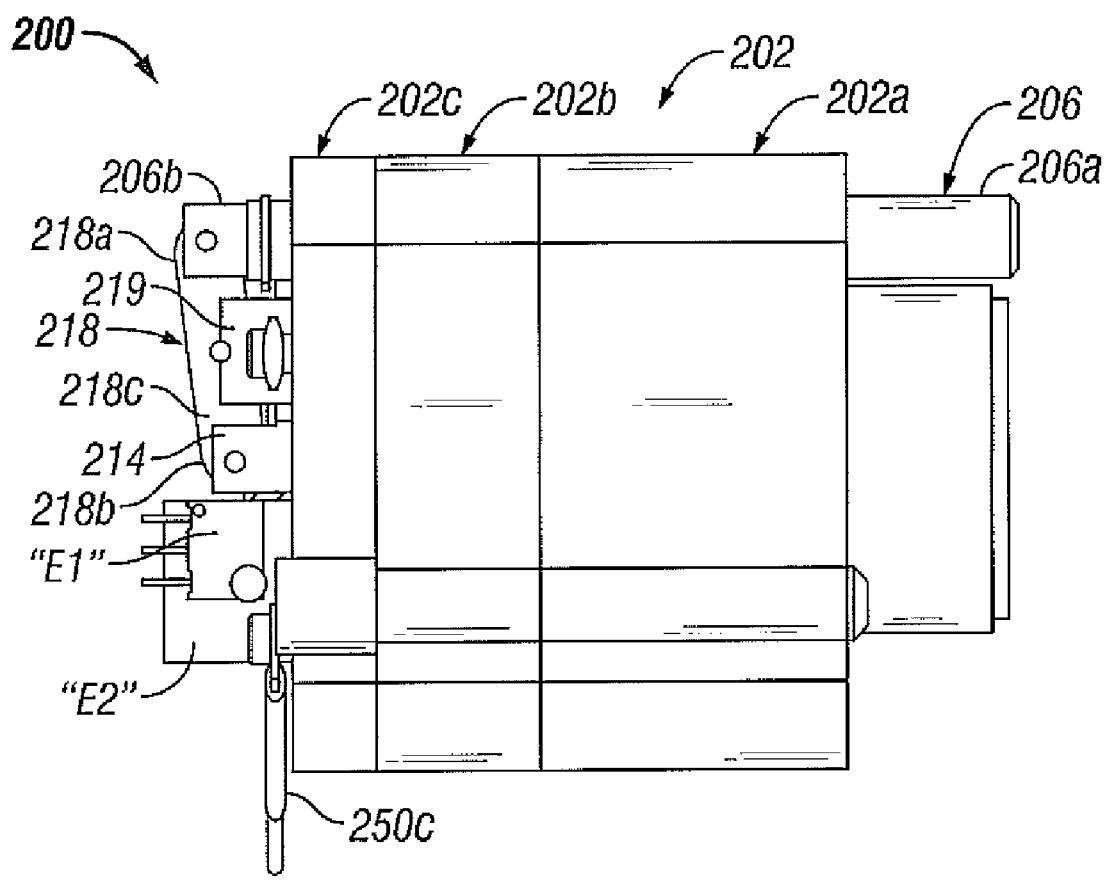
FIG. 6 is a side elevational view of a universal contact port according to another embodiment of the present disclosure.

Various dimensions for ring gear 110 and for spur gears 120a, 120b, 120c are shown in Table A shown in FIG. 6. For example, in one embodiment, ring gear 110 may have an inner diameter of about 0.375 inches, each longitudinal axis "Xa, Xb, and Xc" of spur gears 120a, 120b and 120c may be offset about 0.106 inches from the longitudinal "X" axis, and each spur gear 120a, 120b and 120c may have a diameter of about 0.063 inches to about 0.125 inches.

Turning now to FIGS. 6-11, a universal contact port according to another embodiment of the present disclosure, is generally designated as 200. Universal contact port 200 includes a housing 202 including a distal portion 202a, a middle portion 202b, and a proximal portion 202c. Housing 202 is desirably mounted to an inner surface of electrosurgical generator 14. Housing 202 includes an aperture 204 provided in distal portion 202a which is in registration with an opening provided in electrosurgical generator 14. Aperture 204 is configured to receive contacts 18 or plug 20 of a footswitched accessory 17. (see FIG. 1).

Universal contact port 200 further includes a drive member 206, in the form of an actuator rod, extending through housing 202. Desirably, a distal end 206a of actuator rod 206 projects from or extends through distal portion 202a of housing 202 and through the wall of electrosurgical generator 14. A proximal end 206b of actuator rod 206 extends through proximal portion 202c of housing 202 and defines a clevis 208 or the like.

Figure 7:
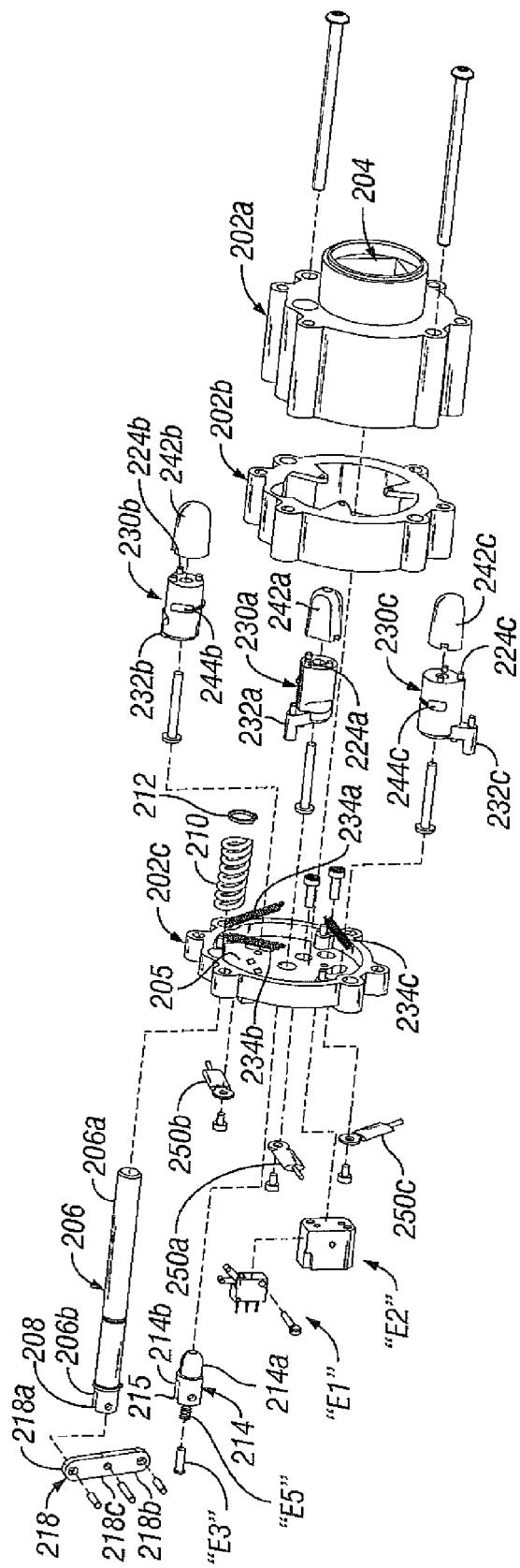
FIG. 7 is a perspective view, with parts separated, of the universal contact port of FIG. 6.
Figure 8:
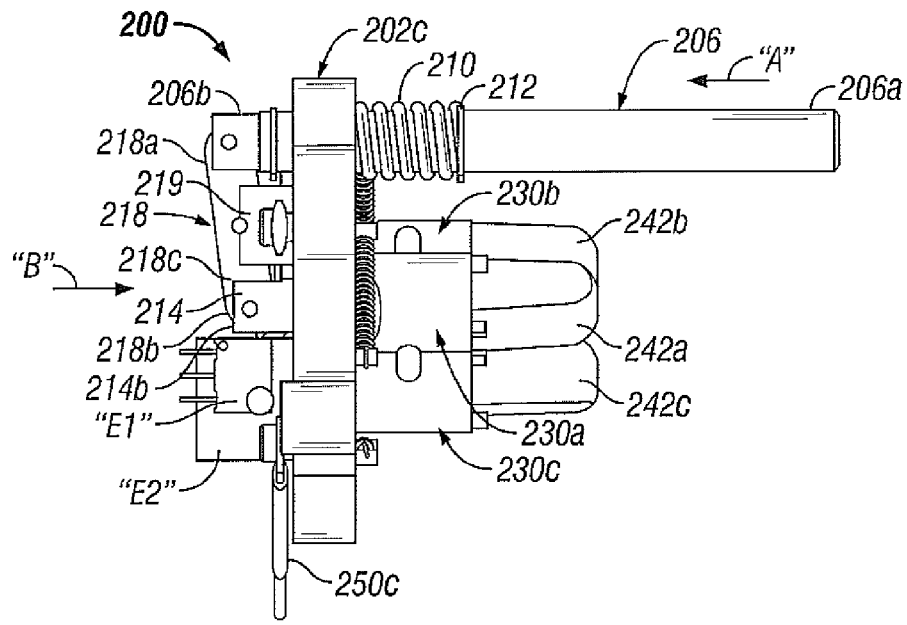
FIG. 8 is a side elevational view of the universal contact port of FIGS. 6 and 7, with the housing removed therefrom.
Figure 11:
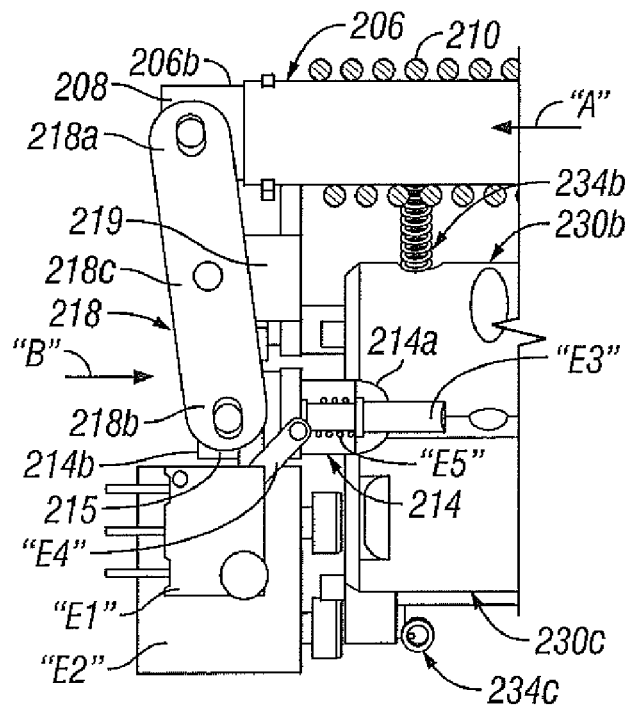
FIG. 11 is a longitudinal cross-sectional view of the universal contact port of FIGS. 6-9, as taken through 11-11 of FIG. 9.

Desirably, as seen in FIGS. 7, 8 and 11, actuator rod 206 is biased to a first un-actuated or un-pressed condition by a biasing member 210 (e.g., a compression spring) or the like. In one embodiment, biasing member 210 is disposed between an inner surface of proximal portion 202c of housing 202 and a C-clamp 212 operatively connected to actuator rod 206.

Universal contact port 200 further includes a pusher member 214 slidably positioned in a central aperture 216 (see FIG. 7) formed in proximal portion 202c of housing 202. Pusher member 214 includes a tapered distal end portion 214a and a proximal end portion 214b defining a clevis 215.

Universal contact port 206 includes a link member 218 operatively interconnecting clevis 208 of actuator rod 206 and to clevis 215 of pusher member 214. Desirably, a first end 218a of link member 218 is pivotally connected to clevis 208 of actuator rod 206 and a second end 218b of link member 218 is pivotally connected to clevis 215 of pusher member 214. Desirably, a central portion 218c of link member 218 is pivotally connected to a stem 219 projecting from proximal portion 202c of housing 202. In this manner, as will be described in greater detail below, as actuator rod 206 is pressed or moved in a proximal direction, as indicated by arrow "A" of FIGS. 9 and 11, link member 218 causes pusher member 214 to move in a distal direction, as indicated by arrow "B" of FIGS. 8 and 11.

Figure 9:
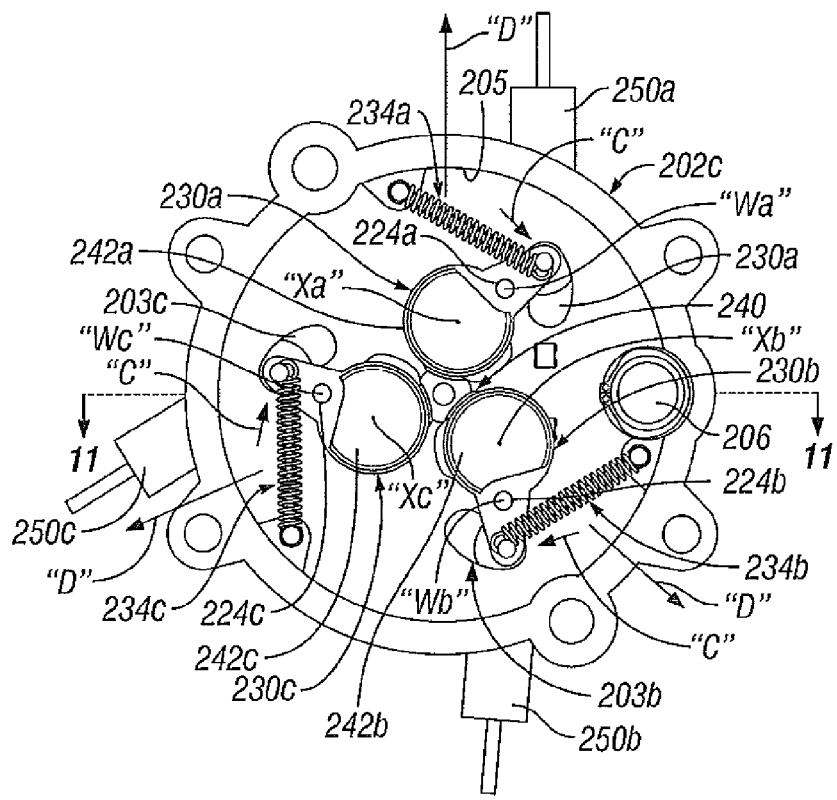
FIG. 9 is a rear elevational view of the universal contact port of FIGS. 6-8, with the housing removed therefrom.
Figure 10:
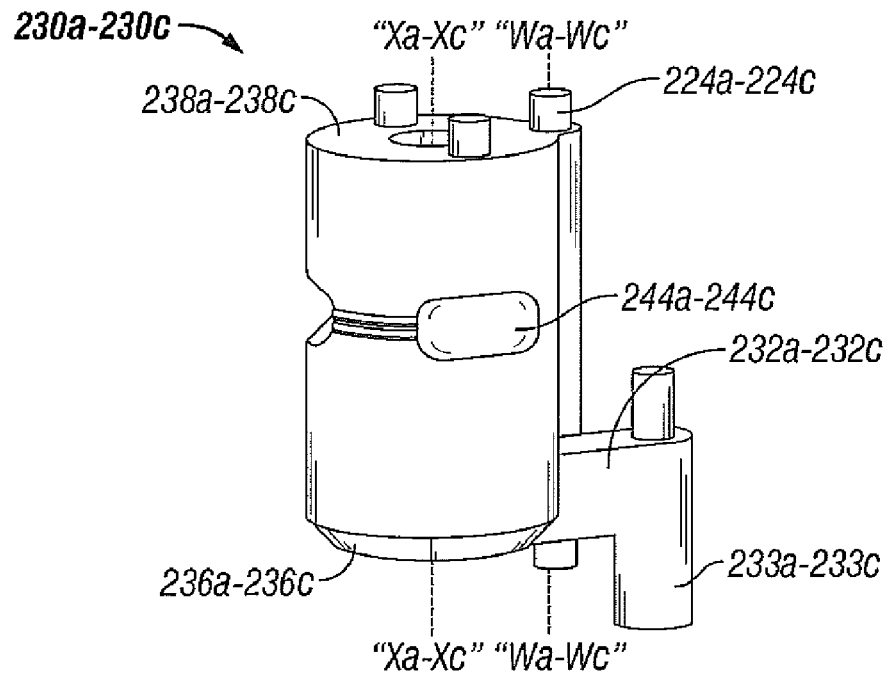
FIG. 10 is a perspective view of a roller of the universal contact port of FIGS. 6-9.

Universal contact port 200 further includes a plurality of rollers 230a-230c eccentrically pivotally supported within housing 202. Desirably, rollers 230a-230c are pivotally supported between middle portion 202b and proximal portion 202c of housing 202. As seen in FIGS. 9 and 10, each roller 230a-230c is substantially cylindrical in configuration and defines a central longitudinal axis "Xa-Xc", respectively.

As seen in FIGS. 7, 9 and 10, each roller 230a-230c includes a shaft or pivot rod 224a-224c, respectively, each defining an axis "Wa-Wc", respectively, about which rollers 230a-230c rotate. Desirably, shafts 224a-224c are pivotally supported in receiving holes or apertures formed in proximal portion 202c and middle portion 202b of housing 202.

As seen in FIG. 9, when rollers 230a-230c are supported in housing 202, rollers 230a-230c define an opening 240 therebetween. Rollers 230a-230c are pivotable between a first position in which rollers 230a-230c are in relative close proximity to one another (i.e., opening 240 is in a constricted condition), and a second position in which rollers 230a-230c are relatively spaced from one another (i.e., opening 240 is in an expanded condition).

As seen in FIGS. 7-10, each roller 230a-230c includes a respective actuation arm 232a-232c extending radially therefrom. As will be described in greater detail below, in operation, as actuation arms 232a-232c are moved in a first direction, as indicated by arrows "C" of FIG. 9, rollers 230a-230c pivot about pivot axes "Wa-Wc" in a second direction, as indicated by arrows "D" of FIG. 9, thereby expanding opening 240. Additionally, it follows that as rollers 230a-230c are pivoted about pivot axes "Wa-Wc", as indicated by arrows "D", thereby expanding opening 240, actuation arms 232a-232c are moved in the direction of arrows "C".

Universal contact port 200 includes a plurality of biasing members 234a-234c (e.g., springs) extending between and connecting a respective actuation arm 232a-232c of rollers 230a-230c to proximal portion 202c of housing 202. In this manner, biasing members 234a-234c maintain rollers 230a-230c in a biased first or constricted condition (i.e., opening 240 is in the constricted condition).

In use, as will be described in greater detail below, when rollers 230a-230c are forced to move in the direction of arrow "D" by movement of pusher member 214 in the direction of arrow "B" (i.e., into opening 240), thereby expanding opening 240, biasing members 234a-234c are stretched or biased. Accordingly, upon movement of pusher member 214 in a direction opposite to arrow "B" (i.e., out of opening 240), biasing members 234a-234c retract, thereby causing rollers 230a-230c to move in a direction opposite to arrow "D" and thus constrict opening 240.

Desirably, as seen in FIG. 10, each roller 230a-230c includes a tapered or angled annular proximal surface 236a-236c, respectively. In operation, when pusher member 214 is moved in a distal direction, tapered distal end portion 214a of pusher member 214 engage and/or cam against tapered proximal surfaces 236a-236c of rollers 230a-230c to radially expand opening 240.

Each roller 230a-230c desirably includes a cap 242a-242c, respectively, operatively connected to or supported on a respective distal end 238a-238c thereof. Each cap 242a-242c may have a tapered configuration or the like.

As seen in FIGS. 7, 9 and 10, each roller 230a-230c includes an electrical contact pad 244a-244c, respectively. Desirably, contact pads 244a-244c are disposed along a side surface of rollers 230a-230c. Preferably, contact pads 244a-244c are positioned on rollers 230a-230c such that contact pads 244a-244c are oriented towards opening 240. In use, as will be described in greater detail below, when contact 18 or plug 20 is inserted into opening 240 and rollers 230a-230c move into contact with contact 18 or plug 20, at least one contact pad 244a-244c, preferably each contact pad 244a-244c, is in electrical engagement with contact 18 or plug 20. When contact pads 244a-244c electrically engage contact 18 or plug 20, an electrical connection between electrosurgical generator 14 and accessory 17 is established.

As seen in FIGS. 7 and 10, each actuation arm 232a-232c of rollers 230a-230c includes a leg 233a-233c, respectively, extending in a proximal direction therefrom. Desirably, each leg 233a-233c extends through a respective slot 203a-203c formed in a rear surface 205 of proximal portion 202c of housing 202.

As seen in FIGS. 6-9, electrical leads 250a-250c are connected to a respective leg 233a-233c of rollers 230a-230c. Desirably, electrical leads 250a-250c are in electrical communication with contact pads 244a-244c of rollers 230a-230c.

As seen in FIGS. 6-8 and 11, universal contact port 200 includes a probe detection switch "E1" operatively supported on proximal portion 202c of housing 202 by a detection switch bracket "E2". Detection switch "E1" functions to alert electrosurgical generator 14 when a particular probe (e.g., contact 18, plug 20, etc.) is operatively connected to universal contact port 200.

In operation, when either contact 18 or plug 20 is inserted into opening 240 of housing 202, a distal end of contact 18 or plug 20 engages (i.e., pushes against) an detection switch actuator pin "E3" which in turn actuates a switch lever arm "E4". Actuation of lever arm "E4" may in turn actuate closure of rollers 230a-230c.

Desirably, a spring "E5" is provided to biasing and/or maintaining actuator pin "E3" and, in turn, lever arm "E4" in an un-actuated condition, thus maintaining rollers 230a-230c in an open condition.

With reference to FIGS. 6-11, a method of using universal contact port 200, for electrically connecting accessory 17 to electrosurgical generator 14, is shown and described. In order to electrically connect accessory 17 to electrosurgical generator 14, actuator rod 206 is pressed and held (i.e., moved in the direction of arrow "A" in FIG. 8) in order to radially expand opening 240 between rollers 230a-230c. In particular, as actuator rod 206 is pressed in the direction of arrow "A", pusher member 214 is moved in a distal direction (i.e., in the direction of arrow "B"), as described in detail hereinabove. Pressing of actuation rod 206 in the proximal direction also results in compression of biasing member 210.

As pusher member 214 moves in the distal direction, tapered distal end portion 214a thereof contacts and/or engages tapered annular surfaces 236a-236c of rollers 230a-230c and forces rollers 230a-230c in a radially outward direction, as indicated by arrows "D" of FIG. 9, thereby radially expanding opening 240. By moving rollers 230a-230c in a radially outward direction, biasing members 234a-234c are stretched, as described in detail hereinabove.

With opening 240 radially expanded, contact 18 or plug 20 of accessory 17 is inserted into opening 240 through aperture 204 (see FIG. 7) of housing 202. Once contact 18 or plug 20 is inserted into opening 240, actuation rod 206 is released. Upon releasing actuation rod 206, biasing member or compression spring 210 is free to expand, thereby forcing actuation rod 206 in a distal direction and thereby forcing pusher member 214 in a proximal direction. As pusher member 214 is forced or moved in a proximal direction, distal end 214a of pusher member 214 is withdrawn from opening 240 (i.e., withdrawn from between rollers 230a-230c).

As pusher member 214 is withdrawn from opening 240, biasing members 234a-234c contract, thereby rotating rollers 230a-230c about their respective pivot axes "Wa-Wc" and constricting opening 240. As opening 240 is constricted, contact pads 244a-244c of respective rollers 230a-230c electrically engage contact 18 or plug 20 thereby completing the electrical connection of accessory 17 to electrosurgical generator 14.

Following the surgical procedure, accessory 17 may be disconnected from electrosurgical generator 14 by simply pulling on contact 18 or plug 20 to thereby withdraw contact 18 or plug 20 from universal contact port 200, or, alternatively, actuation rod 206 may be pressed so as to radially expand opening 240 and thus disengage rollers 230a-230c from contact 18 or plug 20 allowing for contact 18 or plug 20 to be withdrawn from opening 240.

Universal contact ports 100 and 200 enable contacts 18 and/or plugs 20 having a variety of transverse cross-section profiles to be electrically connected to electrosurgical generator 14. For example, contacts 18 or plugs 20 having circular, rectangular, triangular, symmetrical, non-symmetrical, "L-shaped", "V-shaped" and any combination thereof, may be electrically connected to electrosurgical generator 14 using universal contact ports 100 or 200.

It is envisioned and it is in accordance with an embodiment of the present disclosure, that only one of contact pads 244a-244c needs to touch and/or electrically engage contact 18 or plug 20 in order to establish a sufficient electrical connection for operation of accessory 17.

From the foregoing and with reference to the various figure drawings, those skilled in the art will appreciate that certain modifications can also be made to the present disclosure without departing from the scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

The invention claimed is:

1. A universal contact port for use in an electrosurgical generator, the contact port comprising:
   A ring gear having a circular rim formed therein and defining a central rotational axis, the rim including a series of teeth formed therearound;
   A plurality of spur gears operatively engaged with the rim of the ring gear, each spur gear defining a longitudinal axis which is at least substantially parallel with the central rotational axis; and
   At least three rollers operatively associated with a respective spur gear, each roller of the at least three rollers defining a corporal axis, the corporal axis of each roller of the at least three rollers being parallel to an spaced from the longitudinal axis of the respective spur gear, the at least three rollers defining an opening therebetween, wherein the opening is constricted by rotation of the ring gear in a first direction about the central rotational axis and expanded by rotation of the ring gear in a direction opposite to the first direction;
   A plurality of shafts, each shaft of the plurality of shafts configured for eccentrically supporting a respective one of the at least three rollers, wherein the shafts of the at least three rollers are equally spaced from one another,
   wherein each shaft of the plurality of shaft includes a first end operatively associated with a respective spur gear and a second end operatively associated with the electrosurgical generator,
   wherein the opening is at a minimum when the at least three rollers are in contact with one another and wherein the opening is at a maximum when the corporal axes of the at least three rollers are positioned radially outward of the longitudinal axes of the shafts relative to the central axis of the ring gear,
   wherein the at least three rollers are fabricated from electrically conductive material.

2. The universal contact port according to claim 1, wherein the shafts, the spur gears and the ring gear are fabricated from electrically conductive material.

3. The universal contact port according to claim 2, wherein the ring gear and the spur gears define a planetary gear system.

4. The universal contact port according to claim 3, wherein the opening is expandable to receive active contacts of varying diameters therein.

5. The universal contact port according to claim 4, further comprising at least one biasing member operatively associated with at least one of the ring gear, at least one of the spur gears and at least one of the rollers for urging the rollers into contact with one another.

6. The universal contact port according to claim 5, wherein the opening is sizable to receive contacts having cross-sectional diameters from about 2 mm to about 10 mm.

* * * * *

UNITED STATES PATENT AND TRADEMARK OFFICE
CERTIFICATE OF CORRECTION

PATENT NO. : 8,025,660 B2  
APPLICATION NO. : 12/620666  
DATED : September 27, 2011  
INVENTOR(S) : Plaven et al.

Page 1 of 1

It is certified that error appears in the above-identified patent and that said Letters Patent is hereby corrected as shown below:

On the Title Page, paragraph (62), Related U.S. Application Data should be added as follows:

--Divisional of application No. 11/129,985, filed on May 16, 2005, now Patent No. 7,628,786, which claims benefit of Provisional Application No. 60/618,439, filed on October 13, 2004 and claims benefit of Provisional Application No. 60/666,832, filed on March 31, 2005.--

Signed and Sealed this  
Twenty-ninth Day of November, 2011

David J. Kappos  
*Director of the United States Patent and Trademark Office*